(12) United States Patent
Boyce et al.

(10) Patent No.: US 6,808,585 B2
(45) Date of Patent: Oct. 26, 2004

(54) OSTEOGENIC IMPLANTS DERIVED FROM BONE

(75) Inventors: Todd M. Boyce, Aberdeen, NJ (US); David Kaes, Toms River, NJ (US); Nelson L. Scarborough, Ocean, NJ (US)

(73) Assignee: Osteotech, Inc., Eatontown, NJ (US)

( * ) Notice: Subject to any disclaimer, the term of this patent is extended or adjusted under 35 U.S.C. 154(b) by 209 days.

(21) Appl. No.: 09/973,597

(22) Filed: Oct. 9, 2001

(65) Prior Publication Data

US 2002/0035401 A1 Mar. 21, 2002

Related U.S. Application Data

(62) Division of application No. 09/610,026, filed on Jul. 3, 2000.

(51) Int. Cl.⁷ .................................................. A61F 2/28
(52) U.S. Cl. .................. 156/244.11; 156/245; 156/296; 264/109; 623/23.61; 623/23.63; 435/372
(58) Field of Search ............................ 156/244.11, 245, 156/296; 623/23.61, 23.63; 523/113, 115; 435/372; 264/109

(56) References Cited

U.S. PATENT DOCUMENTS

| 4,394,370 A | 7/1983 | Jefferies |
| 4,678,470 A | 7/1987 | Nashef et al. |
| 4,743,259 A | 5/1988 | Bolander et al. |
| 4,902,296 A | 2/1990 | Bolander et al. |
| 4,932,973 A | 6/1990 | Gendler |
| 5,032,445 A | 7/1991 | Scantlebury et al. |
| 5,073,373 A | 12/1991 | O'Leary et al. |
| 5,236,456 A | 8/1993 | O'Leary et al. |
| 5,464,439 A | 11/1995 | Gendler |
| 5,507,813 A | 4/1996 | Dowd et al. |
| 5,556,430 A | 9/1996 | Gendler |
| 5,607,269 A | 3/1997 | Dowd et al. |
| 5,641,518 A | 6/1997 | Badylak et al. |
| 5,683,459 A | 11/1997 | Brekke |
| 5,700,479 A | 12/1997 | Lundgren |
| 5,899,939 A | 5/1999 | Boyce et al. |

FOREIGN PATENT DOCUMENTS

| EP | 0483944 | 5/1992 |
| WO | 97/25941 | 7/1997 |
| WO | 99/39757 | 8/1999 |
| WO | 00/35510 | 6/2000 |
| WO | 00/50102 | 8/2000 |

Primary Examiner—Sam Chuan Yao
(74) Attorney, Agent, or Firm—Dilworth & Barrese LLP (57) ABSTRACT

An osteogenic osteoimplant in the form of a flexible sheet comprising a coherent mass of bone-derived particles, the osteoimplant having a void volume not greater than about 32% and a method of making an osteogenic osteoimplant having not greater than about 32% void volume, the method comprising: providing a coherent mass of bone-derived particles; and, mechanically shaping the coherent mass of bone-derived particles to form an osteogenic osteoimplant in the form of a flexible sheet.

28 Claims, 2 Drawing Sheets

OSTEOGENIC IMPLANTS DERIVED FROM BONE

CROSS REFERENCE TO RELATED APPLICATIONS

This application is a divisional of co-pending U.S. application Ser. No. 09/610,026, filed on Jul. 3, 2000.

BACKGROUND OF THE INVENTION

This invention relates to an osteogenic osteoimplant made up of, at least in part, elongate bone-derived elements intended for use in the repair, replacement and/or augmentation of various portions of animal or human skeletal systems. More particularly, this invention relates to an implant made up of a mass of elongate bone-derived elements optionally in combination with bone powder. The elongate bone-derived elements and/or bone powder may be nondemineralized bone, partially or fully demineralized bone or any combination of the foregoing. An implant of the invention herein is especially suitable for use in periodontal applications, e.g., guided bone regeneration; plastic and reconstructive surgery, e.g., where the contour of the bone must be modified; and filling of cranial defects; though other skeletal applications are also envisioned.

The use of pulverized exogenous bone growth material, e.g., derived from demineralized allogenic or xenogenic bone, in the surgical repair or reconstruction of defective or diseased bone is known. See, in this regard, the disclosures of U.S. Pat. Nos. 4,394,370, 4,440,750, 4,472,840, 4,485,097, 4,678,470, and 4,743,259; Bolander et al., "The Use of Demineralized Bone Matrix in the Repair of Segmental Defects", *The Journal of Bone and Joint Surgery*, Vol. 68-A, No. 8, pp. 1264–1273; Glowacki et al, "Demineralized Bone Implants", *Symposium on Horizons in Plastic Surgery*, Vol. 12, No. 2; pp. 233–241 (1985); Gepstein et al., "Bridging Large Defects in Bone by Demineralized Bone Matrix in the Form of a Powder", *The Journal of Bone and Joint Surgery*, Vol. 69-A, No. 7, pp. 984–991 (1987); Mellonig, "Decalcified Freeze-Dried Bone Allograft as an Implant Material In Human Periodontal Defects", *The International Journal of periodontics and Restorative Dentistry*, pp. 41–45 (June, 1984); Kaban et al., "Treatment of Jaw Defects with Demineralized Bone Implants", *Journal of Oral and Maxillofacial Surgery*, pp.623–626 (Jun. 6, 1989); and, Todescan et al., "A Small Animal Model for Investigating Endosseous Dental Implants: Effect of Graft Materials on Healing of Endosseous, Porous-Surfaced Implants Placed in a Fresh Extraction Socket", *The International Journal of Oral & Maxillofacial Implants* Vol. 2, No. 4, pp. 217–223 (1987).

More recently, processed bone has been developed into new shapes for use in new surgical applications, or as new materials for implants that were historically made of non-biologically derived materials.

U.S. Pat. No. 4,678,470 describes a non-layered osteoimplanting material produced from bone by a process which includes tanning with glutaraldehyde. The bone may be pulverized, used as a large block or machined into a precise shape. The tanning stabilizes the material and also renders it non-antigenic but negatively impacts the osteoinductivity of the product. The bone material may also be demineralized.

U.S. Pat. No. 5,464,439 describes a continuous sheet of completely or partially demineralized natural bone having sufficient flexibility to conform to the implant site.

U.S. Pat. No. 5,556,430 describes the use of a continuous sheet of demineralized bone or partially demineralized bone, however, the sheet must be sufficiently flexible, therefore sacrificing strength, in order to conform to the skeletal site to which it is applied.

U.S. Pat. No. 5,507,813 describes a surgically implantable sheet formed from elongate bone-derived elements, optionally demineralized, containing biocompatible ingredients, adhesives, filler, plasticizers, etc.

U.S. Pat. No. 4,932,973 describes an artificial organic bone matrix with holes or perforations extending into the organic bone material. These holes or perforations are indicated to be centers of cartilage and bone induction following implantation of the bone matrix.

U.S. Pat. No. 4,394,370 describes a one-piece sponge-like osteoimplant material fabricated from filly demineralized bone powder or micro particulate bone, and reconstituted collagen. The sponge-like graft is optionally cross-linked with glutaraldehyde.

Another one-piece porous implant is described in U.S. Pat. No. 5,683,459. The implant is made up of a biodegradable polymeric macrostructure, which is structured as an interconnecting open cell meshwork, and a biodegradable polymeric microstructure composed of chemotactic ground substances such as hyaluronic acid.

U.S. Pat. No. 5,899,939 describes an osteoimplant fabricated from a number of layers possessing compression strength characteristics approximating those of natural bone.

However, the prior art demineralized bone products have proven to be unsatisfactory for applications requiring a thin osteogenic material capable of displaying a variety of properties. In one embodiment of the invention herein, the material is thin and conforming, i.e., able to be shaped closely to the exterior of bony surfaces, thereby minimizing stress on the overlying soft tissues. In a different embodiment of the invention herein, the material is form holding, i.e., able to maintain its three-dimensional architecture even after rehydration and deformation prior to or during implantation. Moreover, prior art products have been limited as to the size and shape of the finished product by the size and type of starting material used to form the product. In every embodiment of the invention herein the size of the implant is limited only by the total amount of starting material available and not by the size and type of starting material. Thus, a thin osteogenic material capable of displaying a variety of properties would be highly desirable.

SUMMARY OF THE INVENTION

Therefore, it is an object of the invention to provide an osteogenic osteoimplant having a void volume of not greater than about 32% prepared by providing, at least in part, elongate bone-derived elements in a coherent mass and mechanically shaping the mass.

It is a further object of the invention to provide an osteogenic osteoimplant made up of, at least in part, elongate bone-derived elements which is capable of being three-dimensionally shaped prior to implantation to provide for, say, the specific architecture of an implant site.

It is a further object of the invention to provide an osteogenic osteoimplant consisting of a laminate formed at least in part from the osteoimplant of the invention herein.

It is a further object of the invention to provide an osteogenic osteoimplant made up of fully demineralized bone elements that is membrane like yet capable of holding its shape and volume despite pressure from overlying gingival tissue, i.e., shape retaining.

It is yet a further object of the invention to provide a highly flexible, highly conformable, osteogenic osteoimplant by adding a bio-compatible fluid carrier to the fully demineralized bone-derived elements, the carrier remaining in the implant even after dehydration.

It is yet a further object of the invention to provide an osteogenic osteoimplant wherein one surface is less penetrable by cells.

It is yet a further object of the invention to provide an osteogenic osteoimplant which can be tailored to have varied permeability and handling characteristics.

It is yet a further object of the invention to provide an osteogenic osteoimplant in which at least one surface can be treated to produce a visible pattern.

It is yet a further object of the invention to provide an osteogenic osteoimplant whose size is limited only by the amount of starting materials available.

In keeping with these and related objects of this invention, there is provided an osteogenic osteoimplant in the form of a flexible sheet having not greater than about 37% void volume comprising a coherent mass of bone-derived particles. This is in contrast to the shaped materials prepared in accordance with U.S. Pat. No. 5,507,813 that have a void volume of at least about 37% and the load-bearing materials prepared in accordance with U.S. patent application Ser. No. 09/256,447 filed Feb. 23, 1997 which have a wet compressive strength of at least about 3 MPa.

Although not wishing to be bound by theory, it is believed that the relatively small void volume of the osteoimplant of this invention allows for the improved properties as compared to like materials that have a void volume of greater than about 32%.

The osteogenic osteoimplant of this invention is much thinner than prior art osteoimplants, i.e., thickness ranging from about 50 microns to about 2000 microns being entirely suitable. In one embodiment, the osteogenic osteoimplant of the invention herein can be contoured to a specific three-dimensional architecture that is retained even after rehydration. This form holding embodiment of the invention is able to be incorporated as a graft into the implant site and retains its architecture even after deformation prior to or during implantation while providing an implant that can interact biologically with the host tissue.

In a different embodiment of the invention, the fully demineralized bone-derived particles, i.e., elongate bone-derived elements and/or bone powder, are combined with a suitable biocompatible fluid carrier that remains in the implant, even after dehydration, to provide a conformable material. This embodiment of the invention does not have a shape memory in contrast to implants made from thin sections of monolithic demineralized bone as disclosed in U.S. Pat. No. 4,932,973 and is therefore able to be shaped closely to the exterior of a bony surface thereby conforming to a bone-grafted surface. Because this embodiment of the osteoimplant is thin and conformable, the osteoimplant minimizes stress on the overlying soft tissues when they are closed over the bone-grafted site. In addition, the thin membrane-like configuration of this embodiment of the invention allows for its placement between other osteoimplant materials, e.g., allograft and/or autograft, and gingival tissues in ridge augmentation and/or periodontal repair procedures. In a preferred embodiment of the invention herein, the fully demineralized bone-derived implant of this invention, acting as an impermeable membrane, serves primarily as a barrier membrane imparting osteogenic osteoimplant like properties while preventing ingrowth of soft tissues. This is especially important in the instance where the tissue cannot be closed completely or tightly over the bone-grafted site, e.g., ridge augmentation. This is in contrast to prior art products whose flexibility is inadequate for use in facilitating closure during such procedures.

In each of the different embodiments of the invention, the osteogenic osteoimplant prepared according to the method of this invention is not limited as to its final size by the anatomic constraints of the bone-derived elements from which it is made, but rather, it is capable of being made to any size so long as an appropriate amount of starting material is available. In addition, each of the different embodiments is flexible when in the hydrated state. The term "flexible" as utilized herein refers to the ability of the unsupported implant to be deformed by the application of a force or combination of forces, e.g., compressive, flexural, etc.

The term "bone" as used herein refers to bone that is cortical, cancellous or cortico-cancellous of autogenous, allogenic, xenogenic or transgenic origin.

The term "demineralized" as used herein refers to bone containing less than its original mineral content and is intended to encompass such expressions as "substantially demineralized", "partially demineralized" and "fully demineralized".

As utilized herein, the expression "superficially demineralized" refers to bone-derived elements possessing at least about 90 weight percent of their original inorganic mineral content, the expression "partially demineralized" refers to bone-derived elements possessing from about 8 to about 90 weight percent of their original inorganic mineral content and the expression "fully demineralized" refers to bone containing less than 8% of its original mineral context.

The term "osteoimplant" as used herein refers to any bone-derived implant prepared in accordance with the embodiments of this invention and therefore is intended to include expressions such as bone membrane, bone graft, etc.

The term "osteogenic" as applied to the osteoimplant of this invention shall be understood as referring to the ability of the osteoimplant to enhance or accelerate the ingrowth of new bone tissue by one or more mechanisms such as osteoinduction and/or osteoconduction.

The term "osteoinductive" as used herein shall be understood to refer to the ability of a substance to recruit and transform cells from the host which have the potential for repairing bone tissue.

The term "osteoconductive" as used herein shall be understood to refer to the ability of a substance to provide biologically inert surfaces which are receptive to the growth of new host bone.

The term "coherent" as applied to the mass of bone-derived elements refers to the ability of the bone-derived elements to adhere to each other either mechanically, e.g., by entanglement, or bending; or, by the use of a biocompatible matrix regardless of whether the mass of bone-derived elements is in the dry or wetted, i.e., hydrated, state.

The expression "mechanically shaping" or expressions of similar import as used herein shall be understood as referring to the application of external forces, e.g., compressive, lateral, etc., to the coherent mass of bone-derived elements through any suitable means, e.g., pressing, rolling, etc.

The expression "void volume" as used herein shall be understood to refer to the amount of non-solid space contained within the implant of this invention and is determined by averaging the area of white space in each field of stained sections of the implant. Such space will be considered to be void volume even if it contains a substance that is liquid at ambient temperature, e.g., 0.5° to 50° C.

The expression "form holding" as applied to this invention refers to the ability of the implant to be deformed prior to or during implantation and then characteristically returning to its original architecture after implantation.

The term "shape retaining" as utilized herein refers to the ability of the implant to maintain a predetermined shape even after its rehydration and/or implantation.

The expression "non-load-bearing" as utilized herein refers to the unsuitability of the invention herein to be utilized in load-bearing applications, i.e., applications where the osteoimplant would be expected to withstand the application of compressive force along its major dimensions. Rather, the invention herein is envisioned as being suitable for those applications where the load applied to the implant, if any, would be largely flexural or tensile in nature. Of course, some compressive force will be applied to the osteoimplant due to the force(s) exerted by the tissue(s) overlying the osteoimplant, however, such force(s) would be applied along the minor dimension and would not be of such magnitude as to be considered as clinically "load-bearing".

The expression "guided bone regeneration" (GBR) or "guided tissue regeneration" (GTR) as applied to this invention refers to the ability of the implant to induce sufficient bone growth before competitive, faster-growing soft tissue and epithelial cells fill the bone repair site.

The term "occluding" as utilized herein shall be understood to refer to any operation or process which reduces the porosity of a region of the ostegenic osteoimplant thus rendering such surface area substantially impermeable to the ingrowth of soft tissue, i.e., undesired cells and soft tissues that are competitive to bone formation.

The term "integral" as utilized herein is intended to differentiate the ostegenic osteoimplant of this invention from osteoimplants which are combined with a separate barrier membrane material. In the instant invention, the osteoimplant and zone of impermeability are integral with one another, i.e., they are indivisibly interconnected so as to form a single, unified whole.

Use of the expression "bone-derived elements" or expressions of like import, shall be understood as referring to pieces of bone in any variety of sizes, thicknesses and configurations including elongate particles, particles, fibers, strips, powders etc., which can be obtained by milling, shaving, cutting or machining whole bone with the proviso that such elements are not envisioned as containing layers as set forth in U.S. Pat. No. 5,899,939.

DETAILED DESCRIPTION OF THE INVENTION

The osteogenic osteoimplant of the present invention comprises an aggregate made up of, at least in part, elongate bone-derived elements having not greater than about 32% void volume.

To fabricate the osteoimplant of this invention, a coherent mass made up of, at least in part, elongate bone-derived elements is first produced followed by mechanically shaping the mass to form the osteogenic osteoimplant. The osteoimplant of this invention can have a wide variety of properties and characteristics depending upon the ratio of elongate bone-derived elements to bone powder and the degree of demineralization of these bone-derived materials. Of course it will be recognized by one skilled in the art to which this invention most closely pertains that the selective addition of bio-compatible matrix as well as any additional treatment(s) of the osteoimplant of this invention before, during, or after processing or, optionally, after processing but before or during implantation will also affect the properties and characteristics of the osteoimplant of this invention. Such routine variation is envisioned as being within the scope of this invention as detailed in the specification and examples herein.

The bone elements-containing osteoimplant fabricated in accordance with this disclosure will typically possess a bone element content ranging from about 5 to about 100 weight percent, preferably from about 20 to about 99 weight percent, and more preferably from about 40 to about 85 weight percent, based on the weight of the coherent mass calculated prior to mechanical shaping of the coherent mass.

In a preferred embodiment, the coherent mass contains at least some partially demineralized content of elongate bone-derived elements and/or bone powder. In this embodiment, the preferred fluid carrier is the water and/or other fluid(s) entrained along with the particles during the processing, e.g., demineralization, of the bone elements prior to the formation of the osteoimplant of this invention. Such fluid carrier is removed by lyophilization of the osteoimplant prior to or during packaging, all though of course it would be entirely suitable to store and/or ship the osteoimplant as is frozen, or, alternatively to remove the fluid carrier by other methods. Optionally, depending upon the binder which may be used, the bone-derived elements may be fully demineralized or fully mineralized or any combination of the two forms. This embodiment of the invention is form holding, i.e., it is able to retain a specific, predetermined, architecture created during formation of the osteoimplant herein, even after rehydration and subsequent deformation which may occur immediately prior to or during implantation. When this embodiment of the osteoimplant is to be employed in a form holding situation, non-demineralized and/or superficially demineralized bone-derived elements can be concentrated in that region of the osteoimplant where the desired form will be maintained. By fabricating the osteogenic osteoimplant from partially demineralized bone elements, the process by which the osteoimplant breaks down would include both remodeling and incorporation with the host bone, while the architecture is maintained throughout the healing process. The partially demineralized bone-derived elements possess osteoinductive properties and are capable of participating in and accelerating the healing process. Malleability and strength are also maintained. Being semi-rigid in nature, the embodiment is ideal for allowing a small amount of necessary movement and load transfer at the repair site.

In yet a further embodiment of this invention, the above osteoimplant can be combined in various ways with other similar osteoimplants or other materials to form an osteoimplant of laminate-type construction. For example, layers of the osteoimplant of the invention herein can be, through chemical or mechanical means, caused to adhere to each other; or, optionally, with other materials, e.g., reinforcing fibers, fabrics, meshes, etc., between some or all of the osteoimplant layers. Such laminate materials will differ from known osteoimplant laminates such as those disclosed in U.S. Pat. No. 5,899,939 in that the final size and architecture will be determined by the total amount of starting donor material available rather than the specific size or shape of the usable donor material available.

For example, in a preferred embodiment of the invention herein, the osteoimplant is formed of elongate bone-derived elements in combination with bone powder. The ratio of elongate bone-derived elements to bone powder is between about 1:0 to about 1:4. The bone elements of this embodiment of the invention will be processed such that the mineral content of the bone elements will be between about 0 and about 100%, based on the original mineral content of the bone elements.

In yet a different embodiment of the invention, the bone elements that comprise the coherent mass, present in the same ratios as described above, will be fully demineralized prior to being mechanically shaped into the osteoimplant of the invention. This embodiment, although being very thin, is relatively inflexible prior to rehydration and is form holding while dry tending to return to its original shape after deformation.

A preferred variation of the above embodiment requires the addition of between about 10 to about 90 percent by weight of the total coherent mass prior to being mechanically shaped of a bio-compatible fluid carrier that remains in the osteoimplant even after dehydration. In this embodiment of the invention, the osteoimplant is thin and without form memory. Therefore this embodiment is conformable and is especially useful in applications requiring an osteoimplant that applies minimal stress, i.e., it does not disrupt the overlying soft tissue that is closed over it. Of course, as is the case for all embodiments of this invention, this particular embodiment can receive further treatment(s), e.g., to render it impermeable to soft tissue ingrowth, resulting in that instance an osteoimplant that readily acts as a barrier membrane.

As stated above, all such combinations and permutations of the bone elements and/or fluid carrier and/or optional materials and/or optional treatments, as well as any suitable method of drying the mechanically shaped osteoimplant, are envisioned as being within the scope of this invention.

After mechanically shaping the osteoimplant of the invention as described above, a region of the osteoimplant may be optionally occluded to reduce the porosity of that region so as to render that region impermeable to the ingrowth of soft tissue. The osteoimplant can also be optionally pre-shaped to a specific form e.g., sheet, plate, dish, tunnel, cone, tube, etc. and/or three-dimensional architecture prior to packaging or immediately prior to implantation. Depending upon the specific embodiment or intended use of the osteoimplant of this invention, optional treatments, e.g., protein modification, addition of biocompatible or bioactive substances, etc., may be provided either before, during, or after production of the osteoimplant. Such optional treatments are envisioned as being within the scope of this invention.

Production of the Coherent Mass of Bone-derived Elements

The bone useful in the invention herein is obtained utilizing methods well known in the art, e.g., aseptically procured allogenic donor bone that has been cleaned and disinfected. Bone-derived elements can be readily obtained from donor bone by any one of several methods, e.g., as described in commonly assigned U.S. patent application Ser. No. 09/211,310, filed Dec. 14, 1998, incorporated herein by reference.

As described in Ser. No. 09/211,310, bone particles generally characterized as "elongate", and therefore useful herein, possess relatively high median length to median thickness ratios. Such elongate particles can be readily obtained by any one of several methods, e.g. by milling or shaving the surface of an entire bone or relatively large section of bone. Employing a milling technique, one can obtain a mass of elongate bone particles containing at least about 60 weight percent, preferably at least about 70 weight percent and most preferably at least about 80 weight percent of bone particles possessing a median length of from about 2 to about 200 mm or more and preferably from about 10 to about 100 mm, a median thickness of from about 0.05 to about 2 mm and preferably from about 0.2 to about 1 mm, and a median width of from about 1 mm to about 20 mm and preferably from about 2 to about 5 mm. These bone particles can possess a median length to median thickness ratio of at least about 50:1 up to about 500:1 or more and preferably from about 50:1 to about 100:1, and a median length to median width ratio of from about 10:1 to about 200:1 and preferably from about 50:1 to about 100:1. Another procedure for obtaining the elongate bone particles herein, particularly useful for pieces of bone of up to about 100 mm in length, is the bone processing mill described in commonly assigned U.S. Pat. No. 5,607,269. Use of this bone mill results in the production of long, thin strips which quickly curl lengthwise to provide tubular-like bone particles. If desired, the mass of bone particles can be graded into different sizes to reduce or eliminate any less desirable size(s) of particles which may be present. In overall appearance, the elongate bone particles can be described as filaments, fibers, threads, slender or narrow strips, etc.

The bone may be cortical, cancellous, or corticocancellous of autogenous, allogenic, xenogenic or transgenic origin.

Mixtures of one or more types of demineralized bone-derived elements can be employed. Moreover, one or more of types of demineralized bone-derived elements can be employed in combination with non-demineralized bone-derived elements, i.e., bone-derived elements that have not been subjected to a demineralization process. Thus, e.g., the weight ratio of non-demineralized to demineralized bone elements can broadly range from about 0:1 to about 1:0. Suitable amounts can be readily determined by those skilled in the art on a case-by-case basis by routine experimentation.

If desired, the bone-derived elements can be modified in one or more ways, e.g., their protein content can be augmented or modified as described in U.S. Pat. Nos. 4,743,259 and 4,902,296, the contents of which are incorporated by reference herein. The bone-derived elements can be admixed with one or more optional substances such as binders, fillers, fibers, meshes, substances providing radiopacity, plasticizers, biostatic/biocidal agents, surface active agents, and the like, prior to, during, or after compressively shaping the particles into a desired configuration. One or more of such substances can be combined with the bone-derived elements by soaking or immersing the bone-derived elements in a solution or dispersion of the desired substance, by physically admixing the bone-derived elements and the desired substance, and the like.

Suitable binders include biological adhesives such as fibrin glue, fibrinogen, thrombin, mussel adhesive protein, silk, elastin, collagen, casein, gelatin, albumin, keratin, chitin or chitosan; cyanoacrylates; epoxy-based compounds; dental resin sealants; bioactive glass ceramics (such as apatite-wollastonite); dental resin cements; glass ionomer cements; nonbioabsorbable polymer such as polyacrylate, polymethyl methacrylate, polytetrafluroethylene, polyurethane, polyamide; gelatin-resorcinol-formaldehyde glues; collagen-based glues; acrylic resins; bioabsorbable polymers such as starches, polyglycolide, polylactide, glycolide-lactide copolymers, polycaprolactone, polycarboxylic acids and their copolymers, polycarbonates, polyorthoesters, polyamino acids, polycyanoacrylates, polyhydroxybutyrate, polyhydroxyvalyrate, polyphosphazenes, polyvinylpyrrolidone, poly-propylene fumarate, poly-propylene fumarate-diacrylate, poly (propylene glycol-co-fumaric acid), tyrosine-based polycarbonates, pharmaceutical tablet binders (such as Eudragit® binders available from Hulls America, Inc.), polyvinylpyrrolidone, cellulose, ethyl cellulose, microcrystalline cellulose and blends thereof; nonbioabsorbable polymers such as polyacrylate, polymethylmethacrylate, polytetrafluroethylene, polyurethane and polyamide; etc., derivatives and blends of the foregoing are also suitable. When employed, binder will typically represent from about 1 to about 40 weight percent of the bone particle containing composition, calculated prior to forming the shaped material. The preferred binder is glycolide-lactide copolymer.

Suitable fillers include graphite or pyrolytic carbon; bioceramics; bone powder; fully mineralized and partially or fully demineralized cortical and cancellous bone in any form, including particles such as demineralized bone powder (or "demineralized bone matrix" as it may also be called); sheets and shaped bone pieces; bioglass or other bioceramic or natural or synthetic polymers, e.g., bioabsorbable polymers such as polyglycolide, polylactide, glycolide-lactide copolymer, and the like; nonbioabsorbable materials such as starches, polymethyl methacrylate, polytetrafluoroethylene, polyurethane, polyethylene and nylon; anorganic bone (i.e., bone mineral only, with the organic constituents removed), dentin tooth enamel, aragonite, calcite, nacre, amorphous Calcium phosphate, hydroxyapatite, Tricalcium phosphate and other Calcium phosphate materials; Calcium salts; etc. and mixtures of any of the foregoing. When employed, filler will typically represent from about 1 to about 50 weight percent of the bone particle containing composition, calculated prior to forming the shaped material. The preferred fillers are ceramics, particularly hydroxyapatite and mineralized cortical bone powder.

Suitable fibers include carbon fibers (graphite or diamond); collagen fibers; tendon or ligament derived fibers; keratin; catgut; silk; cellulose; chitosan; suture materials, e.g., PLA/PGA and other copolymers; polyethylene; Teflon®; polyurethanes; Bioglass®; hydroxyapatite and other Calcium phosphate materials in whisker or fiber shape; Aluminum oxide; etc. When employed, fiber will typically represent from about 1 to about 30 weight percent of the bone particle containing composition, calculated prior to forming the shaped material. The preferred fiber is collagen fibers.

Examples of meshes include for example, fabric or mesh structures containing the above identified fibers; metallic meshes, e.g., Titanium and alloys, Tantalum, stainless steels, Cobalt chrome alloys, Gold, Silver, Platinum; etc. When employed, mesh will typically represent from about 1 to about 7 weight percent of the bone particle containing composition, calculated prior to forming the shaped material. The preferred mesh is titanium mesh.

Examples of substances imparting radiopacity include for example, fully mineralized bone particles, Barium and Iodine containing compounds or compositions, e.g., Barium Sulfate and Barium Sulfate for Suspension, Iopanoic Acid, and the like. When employed, substances imparting radiopacity will typically represent from about 1 to about 25 weight percent of the bone particle containing composition, calculated prior to forming the shaped material. The preferred substance imparting radioapacity is barium sulfate.

Suitable plasticizers include liquid polyhydroxy compounds such as glycerol, monoacetin, diacetin, pluronics, polyoxymers, block copolymers, oils, gels of colloidal clays, aqueous gels of organic polymers such as gelatin, pectin, methyl cellulose and high-molecular-weight polyethylene glycol; thixotropic agents such as aluminum hydroxide gel and aluminum phosphate gel, solution of polyvinyl alcohol, polyvinylpyrrolidone, cellulosic ester such as hydroxypropyl methylcellulose, carboxyl methylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, hydrogels, gels of colloidal clays, aqueous gels of organic polymers, such as gelatin agar, pectin methylcellulose, and high-molecular-weight polyethylene glycol, chitosan, other materials that can suspend particles; etc. When employed, plasticizer will typically represent from about 10 to about 90 weight percent of the bone particle containing composition, calculated prior to forming the shaped material. The preferred plasticizers is glycerol.

Suitable biostatic/biocidal agents include antibiotics, povidone, sugars, mucopolysaccharides, chlorobutanol, quarternary ammonium compounds such as benzalkonium chloride, organic mercurials, parahydroxy benzoates, aromatic alcohols, halogenated phenols, sorbic acid, benzoic acid, dioxin, EDTA, BHT, BHA, TBHQ, gallate esters, NDGA, tocopherols, gum guaiac, lecithin, boric acid, citric acid, p-Hydroxy benzoic acid esters, propionates, Sulfur dioxide and sulfites, nitrates and nitrites of Potassium and Sodium, diethyl pyrocarbonate, Sodium diacetate, diphenyl, hexamethylene tetramine o-phenyl phenol, and Sodium o-phenylphenoxide, etc. When employed, biostatic/biocidal agent will typically represent from about 1 to about 25 weight percent of the bone particle containing composition, calculated prior to forming the shaped material. The preferred biostatic/biocidal agent is antibiotic drugs.

Suitable surface active agents include the biocompatible nonionic, cationic, anionic and amphoteric surfactants and mixtures thereof. When employed, surface active agent will typically represent from about 1 to about 20 weight percent of the bone particle containing composition, calculated prior to forming the shaped material.

It will be understood by those skilled in the art that the foregoing list of optional substances is not intended to be exhaustive and that other materials may be admixed with bone-derived elements within the practice of the present invention.

Any of a variety of medically and/or surgically useful optional substances can be incorporated in, or associated with, the bone-derived elements either before, during, or after preparation of the osteogenic osteoimplant. Thus, e.g., one or more of such substances can be introduced into the bone-derived elements, e.g., by soaking or immersing the bone-derived elements in a solution or dispersion of the desired substance(s), by adding the substance(s) to the carrier component of the osteogenic osteoimplant or by adding the substance(s) directly to the osteogenic osteoimplant. Medically/surgically useful substances include physiologically or pharmacologically active substances that act locally or systemically in the host.

The medically/surgically useful substances are bioactive substances which can be readily combined with the bone-derived elements, fluid carrier and/or osteogenic osteoimplant of this invention and include, e.g., demineralized bone powder as described in U.S. Pat. No. 5,073,373 the contents of which are incorporated herein by reference; collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as alkaline phosphatase, collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors or other means; tissue transplants; demineralized bone powder; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interlenkins, e.g., interleukin-1 (IL-1), interleukin-2 (IL-2); human alpha thrombin; transforming growth factor (TGF-beta); insulin-like growth factors (IGF-1, IGF-2); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids. The amounts of such optionally added substances can vary widely with optimum levels being readily determined in a specific case by routine experimentation.

It will be understood by those skilled in the art that the foregoing list of medically/surgically useful substances is not intended to be exhaustive and that other useful substances may be admixed with bone particles within the practice of the present invention.

The total amount of such optionally added medically/surgically useful substances will typically range from about 0 to about 95, preferably from about 1 to about 60, more preferably from about 1 to about 40 weight percent based on the weight of the entire composition prior to compression of the composition, with optimal levels being readily determined in a specific case by routine experimentation. The preferred medically/surgically useful substance is bone morphogenic proteins.

The mass of bone-derived elements of this invention can be freshly prepared just by mixing desired quantities of the bone-derived elements, fluid carrier, if any, and optional component(s), if any, in any suitable sequence of separate mixing operations or all at once. Thus, the bone-derived elements, can be mixed with the optional component(s) and thereafter combined with the fluid carrier component, the bone-derived elements can be mixed with the fluid carrier followed by addition of the optional ingredient(s) or the optional ingredients can be added to the fluid carrier followed by addition of the bone-derived elements. Variations of these and other sequences of mixing are, of course, possible. Advantageously, the bone-derived elements, fluid carrier and optional ingredient(s) are mixed substantially simultaneously such that the particles of the osteogenic osteoimplant are entangled.

One method of fabricating the bone-element containing coherent mass which can be advantageously utilized herein involves contacting a quantity of bone-derived elements, of which at least about 25 weight percent preferably constitute fully-demineralized elongate bone particles as described above, with a sufficient amount of a suitable biocompatible fluid carrier, e.g., water, organic protic solvent, aqueous solution such as physiological saline, liquid polyhydroxy compounds, etc. (the carrier can optionally contain one or more substances such as described above) to form a dough-like composition. The carrier may already be present after the demineralization step. In such a case, no additional carrier need be added. Suitable biocompatible fluid carriers are known in the art and are described in U.S. Prov. Appl. No. 60/159,774 filed Oct. 15, 1999, the contents of which are incorporated herein.

In a preferred embodiment of the invention herein, the liquid carrier is a liquid polyhydroxy compound, liquid polyhydroxy compound derivative, liquid solution of solid polyhydroxy compound, liquid solution of solid polyhydroxy compound derivative or mixtures thereof. If necessary or desirable, the liquid carrier can be dissolved or diluted with an appropriate solvent such that when combined with the bone-derived elements of the invention a bone element-containing composition capable of being shaped is provided. Thus, the polyhydroxy compound or polyhydroxy derivatives can be a liquid in the pure or highly concentrated state at ambient temperature, e.g., 0.5° to 50° C., or it can be a solid or semi-solid at this temperature in which case it becomes necessary to dissolve the material in a solvent such as water, physiological saline, ethanol, glycerol, glucose, propylene glycol, polyethylene glycol of from 200–1000 molecular weight, polyvinyl alcohol, etc. Of course, the liquid carrier can be made up of one or more liquid polyhydroxy compounds or derivatives in solution with one or more solid polyhdroxy compounds or derivatives. Likewise, the liquid carrier can be made up of a polymer and/or polymeric mixture of any of the suitable compounds mentioned herein. Most preferred is a 50% (v/v) aqueous solution of glycerol.

Where, in a particular embodiment, the particles exhibit a tendency to quickly or prematurely separate from the carrier component or to otherwise settle out from the composition such that preparation of a fairly homogeneous coherent mass is rendered difficult or inconvenient, it can be advantageous to include within the composition which forms the osteogenic osteoimplant an optional substance whose thixotropic characteristics prevent or reduce this tendency. Thus, e.g., where the carrier component is glycerol or a solution of glycerol in a solvent, such as an aqueous or alcoholic solution of glycerol, and separation of bone-derived elements occurs to an excessive extent where a particular application is concerned, a thixotropic agent such as described above can be combined with the carrier in an amount sufficient to significantly improve the suspension-keeping characteristics of the composition.

The amount of elongate bone-derived elements which can be incorporated into the osteogenic osteoimplant of the invention can vary widely with amounts of from 10 to about 100 weight percent, and preferably from about 20 to about 70 weight percent, being entirely suitable in most cases. Likewise, the amount of the bone powder which can be incorporated into the osteogenic osteoimplant can very widely with amounts from about 90 to about 0 weight percent, and preferably from about 80 to about 30 weight percent, being entirely suitable in most cases. The ratio of elongate bone-derived elements to bone powder can vary between about 1:0 to about 1:9. The balance of the osteoimplant being made up of fluid carrier and optional ingredient (s), if any.

In one embodiment of the invention, the osteoimplant is formed from fully demineralized bone-derived elements in combination with a suitable bio-compatible fluid carrier. A preferred bio-compatible fluid carrier is an aqueous solution of glycerol, e.g., 50% glycerol (v/v). This embodiment of the invention results in an osteoimplant that is conformable and can be further subjected to surface treatment, e.g., occluding a surface, to form an osteoimplant especially suitable to barrier membrane applications. In another embodiment of the invention, the osteogenic osteoimplant is formed from, at least in part, elongate bone-derived elements in combination with water and/or physiologic saline as the fluid carrier and/or binder. This results in an embodiment of the invention that is capable of being configured to a specific three-dimensional architecture, the architecture being retained even after rehydration and deformation prior to or during implantation. Thus, the amount and type of bone elements and/or fluid carrier and/or binder can be varied depending upon the intended final use of the osteoimplant.

Forming the Osteoimplant

To form the osteogenic osteoimplant of this invention a coherent mass of bone-derived elements prepared as described above is subjected to mechanical shaping. Such shaping is accomplished through the application of compressive and, optionally, simultaneous lateral force(s). Because the coherent mass can display viscoelastic properties, the force required to deform the mass is sensitive to the rate of application and is readily determined by routine experimentation. The application of this force(s) can be accomplished by a variety of methods, e.g., pressing, extruding, rolling, etc. When necessary to prevent the mass from sticking to the work surface and/or roller(s), the coherent mass may be placed between two flexible stick-resistant surfaces, e.g., Tyvek™ sheets, or a Teflon™ coated surface.

In a preferred embodiment the coherent mass is placed on an inflexible, impermeable, horizontally planar work surface and then compressively contacted with a revolving impermeable cylindrical roller with such force being applied as is necessary to form an osteoimplant of the desired characteristics. Alternatively, the coherent mass can be subjected to a series of successive contacts with two or multiples of two parallel rollers rotating counter directionally with respect to each other and such a distance apart from each other that an osteoimplant of desired thickness is formed. Such rollers can include roller(s) modified to provide for the surface treatment of one or both surfaces of the osteoimplant, e.g., rollers having a patterned surface; rollers that are barrel-shaped to provide curvature to the shaped material; rollers that may emboss a design or texture to the osteoimplant; rollers that may imprint a series of perforations or penetrating holes for sizing of the sheets, i.e., a cutting guide or to improve biological ingrowth; rollers that are heated; rollers containing raised cutters to section pieces; etc. The rollers can also be modified to create moderate to large pores through the material thereby creating a mesh-like material, such a mesh-like implant can also be provide utilizing any standard technique, e.g. weaving, expanding, etc.

The osteogenic osteoimplant can then be used immediately, subjected to optional treatment(s), e.g., tissue engineering methods may be employed to grow living cells within the matrix of the invention prior to surgical implantation, if any, or preferably dehydrated, e.g., lyophilized, and/or frozen prior to packaging for use. The osteoimplant can optionally be dried using any method(s) that provides a finished osteoimplant in compliance with American Association of Tissue Banks requirements.

Optionally Occluding a Portion of the Surface Area of the Osteogenic Osteoimplant When the osteogenic osteoimplant of the invention is intended to be used in barrier membrane applications, the resulting osteoimplant is optionally subjected to an operation or process which occludes a selected surface area of the osteoimplant to provide a skin or barrier which is impermeable to soft tissue ingrowth. This operation can be performed by heating a portion of the surface area of the osteoimplant, by cross-linking a portion of the surface area of the osteoimplant and/or by applying one or more biocompatible substances to a portion of the surface area of the osteoimplant to provide a microporous layer thereon. It will be understood by those skilled in the art that combinations of one or more of the foregoing operations can be employed, e.g., heating followed by cross-linking, cross-linking followed by heating, cross-linking followed by application of biocompatible substance, etc. It will also be understood by those skilled in the art that any of these operations can be performed on the osteoimplant before or after the optional drying and/or lyophilizing steps described above. Thus, e.g., the osteoimplant can be subjected to the heating operation to occlude a portion of the surface area of the osteoimplant followed by lyophilization of the occluded osteoimplant. Such barrier forming operations are known and disclosed in commonly assigned U.S. patent application Ser. No. 09/211, 310 filed Dec. 14, 1998 the contents of which are incorporated herein by reference.

Optionally Shaping the Osteogenic Osteoimplant

The resulting osteogenic osteoimplant can assume a determined or regular form or configuration such as a sheet, plate, disk, tunnel, cone, tube, to name but a few. Prefabricated geometry would include, but not be limited to, a crescent apron for single site use, an I-shape to be placed between teeth for intra bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, wave plates, etc. Partial tubular as well as flat plates can be fabricated from the osteoimplant of this invention. Such plates may include such conformations as, e.g., concave contoured, bowl shaped, defect shaped, etc. Of course, the osteoimplant can be machined or shaped by any suitable mechanical shaping means. Computerized modeling can, for example, be employed to provide for the intricately-shaped three-dimensional architecture of an osteoimplant which is custom-fitted to the bone repair site with great precision.

Optionally, the partially demineralized osteoimplant can be formed into a laminate. Advantages of a laminate of the partially demineralized osteoimplant would include: a.) allowing the laminate to be shaped in three dimensions, as in the introduction of a concave surface shape, etc.; b.) each layer of the laminate would be continuous, without requiring binding of the joints between the pieces. A laminate prepared according to the invention herein would provide a more uniform and stronger laminate osteoimplant than those that are available utilizing prior art methods.

Assembling the superimposed layers into a strong unitary structure can be accomplished by a variety of means/procedures, e.g., application of known and conventional biologically compatible adhesives such as the cyanoacrylates; epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, etc., and protein-based binders such as fibrin glues and mussel-derived adhesive proteins; the use of mechanical fasteners such as pins, screws, dowels, etc., which can be fabricated from natural or synthetic materials and bioabsorbable as well as nonbioabsorbable materials; laser tissue welding; and, ultrasonic bonding. If desired, the layers of the osteogenic osteoimplant can be provided with mechanically interengaging features, e.g., tongue-and-groove, mortise-and-tenon, or dove-tail elements, to facilitate their assembly into the final product and/or to fix the layers to each other in a more secure fashion. The optimal method of assembly would be determined on a case-by-case basis through routine experimentation. In addition to its bone membrane layers, the osteoimplant of this embodiment of the invention can optionally possess one or more layers formed from one or more other materials or substances such as those described above.

Use of the Osteogenic Osteoimplant

The osteogenic osteoimplant of this invention is intended to be applied at a bone repair site, e.g., one resulting from injury, defect brought about during the course of surgery, infection, malignancy or developmental malformation. The osteoimplant can be utilized in a wide variety of orthopedic, periodontal, neurosurgical, oral and maxillofacial surgical procedures such as the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic procedures; etc. Specific bones which can be repaired or replaced with the osteoimplant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones.

Possible clinical applications would include, e.g., the treatment of traumatic fractures, pathologic fractures, stress fractures, congential defects or fractures, or operative defects in any bone of the body that would be treated with plate fixation. Fracture categories treated with the osteoimplant can include but not be limited to intraarticular or periarticular fractures; metaphyseal fractures; transverse, oblique, comminuted, and fragmented fractures; repair to non-fractured sites; defects due to periodontal disease or surgery; and other bone defects.

At the bone repair site, the osteogenic osteoimplant can be employed in the dry or hydrated state. The dry or hydrated osteoimplant can be cut or sized if need be to conform to the site being repaired. The osteoimplant can be hydrated before, during or after implantation with a suitable biocompatible liquid, e.g., water, saline solution, etc., for a period of time ranging from about 1 to about 120 minutes, depending on the thickness of the osteoimplant. After being hydrated, a preferred embodiment of the osteoimplant becomes flexible yet retains its shape and much of its tensile strength. The osteoimplant can be packaged in either the dried or wet state and stored for subsequent application. In some circumstances, it is preferable to package the osteoimplant in the wet state so that it is ready for immediate use at the surgical site. Optional materials can also be added prior to packaging. Preferably the osteoimplant is lyophilized or otherwise dehydrated and/or frozen prior to storage.

At the time just prior to when the osteoimplant of the invention is to be placed in a defect site, optional materials, e.g., autograft bone marrow aspirate, autograft bone, preparations of selected autograft cells, autograft cells containing genes encoding bone promoting action, etc., can be combined with the osteoimplant of this invention. The osteoimplant can be implanted at the bone repair site, if desired, using any suitable affixation means, e.g., sutures, staples, bioadhesives, screws, pins, rivets, other fasteners and the like or it may be retained in place by the closing of the soft tissues around it.

Figure 1:
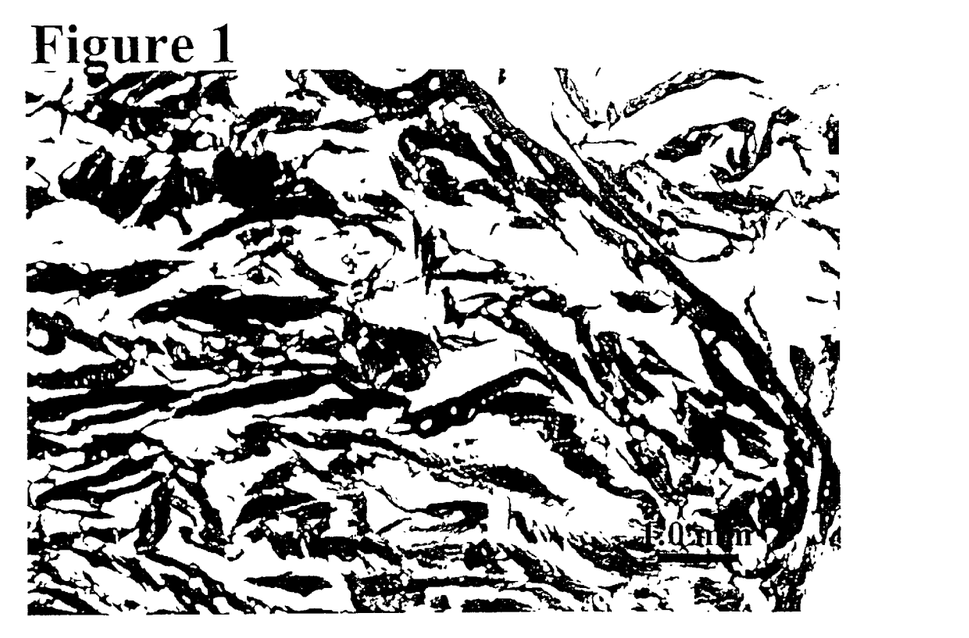
FIG. 1 is cross-sectional view of a shaped material prepared according to U.S. Pat. No. 5,507,813.
Figure 2:
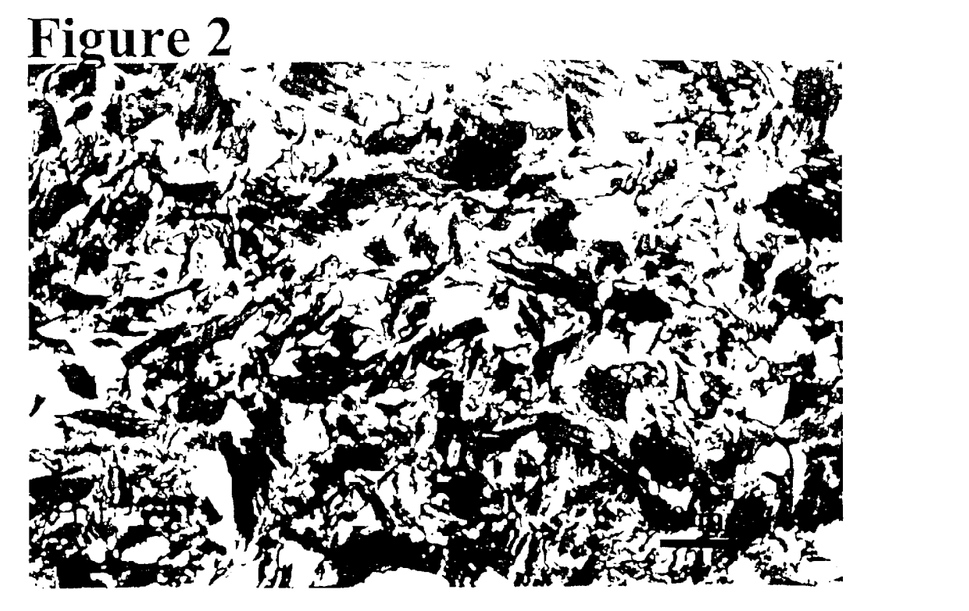
FIG. 2 is a cross-sectional view of an osteogenic osteoimplant prepared according to Example 2 herein.

Turning now to the figures. FIG. 1 is a cross-sectional view of a shaped material prepared according to U.S. Pat. No. 5,507,813. The section is stained to show the presence of bone particles and powder as well as void space. The dark areas of the figure are stained bone material, the white area is the void space contained within the shaped material. FIG. 2 is a cross-sectional view of an osteogenic osteoimplant prepared as described in example 2 herein and stained in the same manner as FIG. 1. A comparison of FIG. 2 with FIG. 1 reveals that the osteoimplant of the invention herein has 42% less void space than the material of FIG. 1. The lesser void space proceeds partially from the greater packing efficiency achieved through the use of small bone particles to fill the spaces left between the larger elongate particles as well as the force(s) applied in the forming of the osteogenic osteoimplant.

Figure 3:
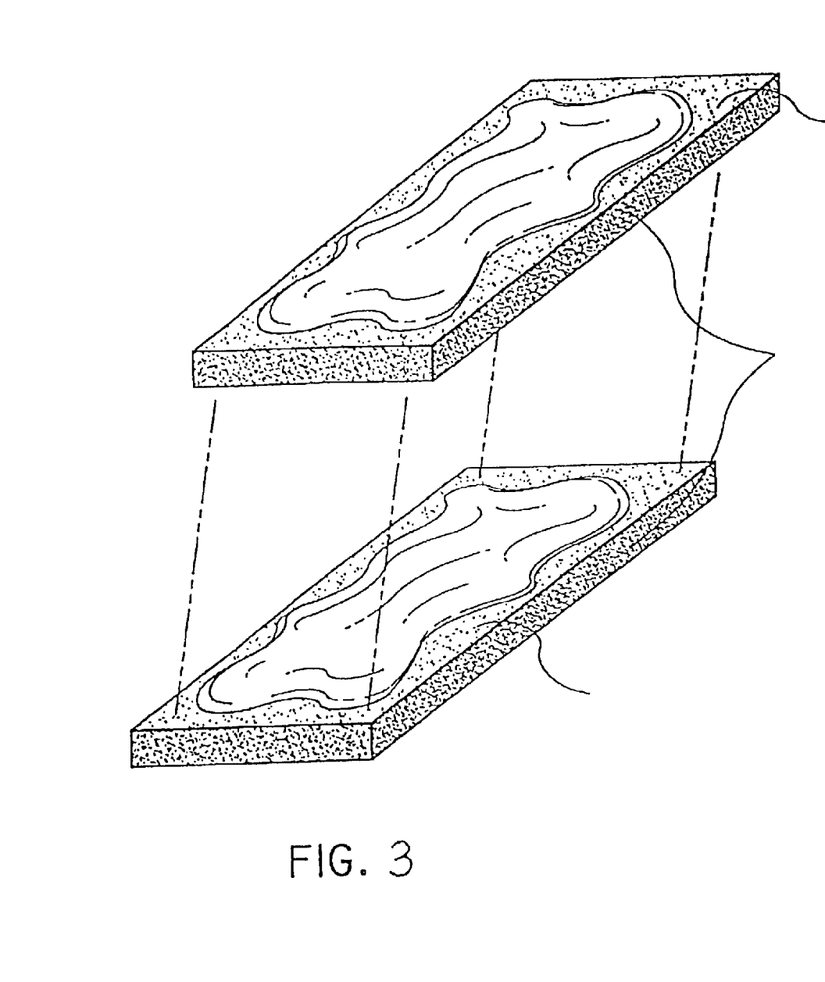
FIG. 3 is an enlarged perspective view of the assembly of a bone-derived laminate implant of the invention herein possessing layers of partially demineralized shaped bone material alternating with other layers of partially demineralized shaped bone material and/or optional materials.
Figure 4:
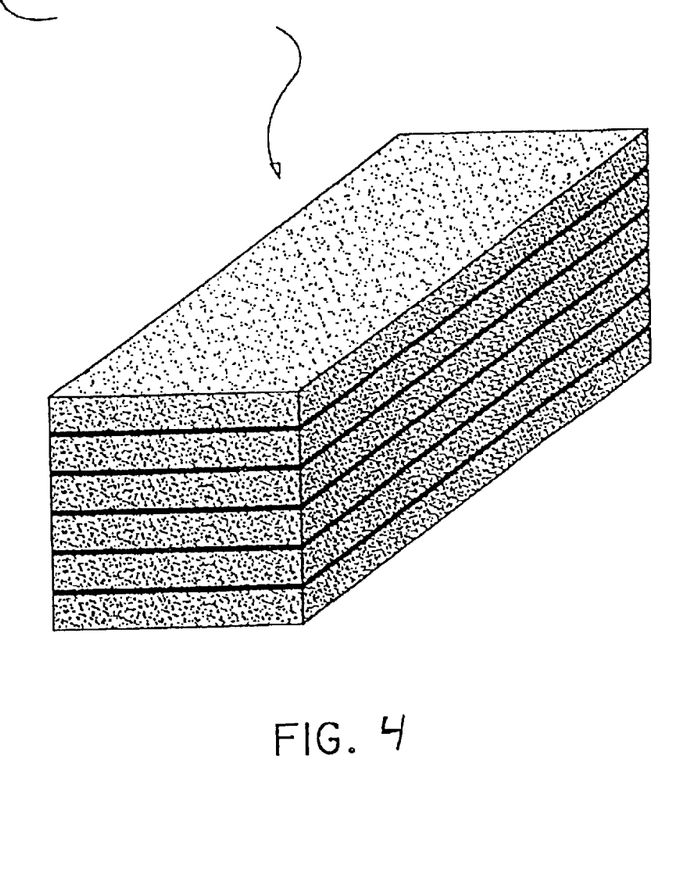
FIG. 4 is an enlarged perspective view of a bone derived laminate of the invention.

FIG. 3 is an enlarged perspective view demonstrating one method of assembling layers of the partially demineralized embodiment of the osteoimplant of the invention to yield the finished laminate depicted in FIG. 4. As shown in the figures, the laminate can be composed of alternating layers having the same or different properties or comprising the same or different materials.

The invention will be more fully understood by way of the following examples which are intended to illustrate but not limit methods of preparation of the osteogenic osteoimplant in accordance with the present invention.

EXAMPLE 1

Allogenic cortical bone was processed in the bone milling apparatus described in U.S. Pat. No. 5,607,269 to yield a mass of bone-derived elements. The bone-derived elements were then placed in a reactor. A 0.6 N solution of HCl at 15 ml per gram of bone-derived elements was introduced into the reactor, the reaction proceeding for 1 to 2 hours. Following drainage of the HCl, the bone-derived elements were covered with 0.6 N HCl/20 ppm-2000 ppm nonionic surfactant solution for 24 to 48 hours. Following drainage of the HCl/surfactant solution, 0.6 N HCl at 15 ml per gram of total bone was introduced into the reactor, the reaction proceeding for 40 to 50 minutes. Following drainage through a sieve, the bone was rinsed three times with water for injection at 15 ml per gram bone weight with the water for injection being replaced at 15-minute intervals. Following drainage of the water for injection, the bone was covered with alcohol and allowed to soak for at least 30 minutes. The alcohol was then drained and the bone was rinsed with water for injection. After draining, the bone elements were transferred to a lyophilization tray and frozen at −70° C. for at least 6 hours. The osteoimplant was then lyophilized following standard procedures for 24 to 48 hours.

EXAMPLE 2

A mass of processed demineralized bovine bone bone-derived elements prepared as described in Example 1 was combined with a sufficient quantity of bio-compatible carrier (50% by weight Glycerol/Water) to yield a coherent mass having a dough-like consistency. The coherent mass was placed on a Tyvek™ sheet that covered an impermeable, horizontally planar work surface. After placing a second sheet of Tyvek™ on top of the coherent mass, the mass was compressively contacted by hand with a revolving 2058 gram, 6.13 cm. diameter, 25.5 cm. long impermeable cylinder with sufficient applied force to yield an osteoimplant having minimal thickness.

COMPARATIVE EXAMPLE 1

A shaped implant prepared from processed demineralized bovine bone according to U.S. Pat. No. 5,507,813 and an osteoimplant prepared as in Example 2 above were prepared in the laboratory. Approximately one-centimeter square pieces were cut from each and prepared for microscopic histological analysis. The tissue was fixed in 10% neutral buffered Formalin, dehydrated in graded alcohols and embedded in the commercially available glycol methacrylate, JB-4 Plus Embedding Kit (Polysciences, Inc.), according to the manufacturer's protocol. Blocks were first trimmed to full face with a Buehler Isomet 2000 equipped with a diamond-wafering blade. Five $\mu$m sections were then cut on a Reichert Jung Autocut 2040 microtome equipped with a 16 cm, D-profile tungsten carbide knife. Sections were stained in a 1% Toluidine Blue, 1% Sodium Borate solution, dehydrated and coverslipped.

The images shown in FIG. 1 (U.S. Pat. No. 5,507,813 ) and FIG. 2 (the osteoimplant prepared according to Example 2 above) were captured using a Nikon Diaphot 300 microscope, a 2× objective and a Kodak DCS 420 Digital Camera. The demineralized bone material (DBM) in each field is dark while the empty spaces appear bright white from the light of the microscope. Six fields from each material were captured. Images were acquired by the image analysis program, Image Pro Plus 3.0 (Media Cybernetics). This program was used to automatically measure the area (in number of pixels) of bright objects by what is essentially a threshold measurement. The area measurement of the bright objects is considered equivalent to the porosity of the DBM matrix. Six fields from each sample type were analyzed in this manner. A student's t-test was used to test for a significant difference between the empty area measurements of the material made according to U.S. Pat. No. 5,507,813 (FIG. 1) and those of the material made according to Example 2 above (FIG. 2). The porosity was expressed as the percentage of empty space divided by the total area analyzed for the sum of the six fields measured, for each of the test materials. The results are given in Table 1 below.

TABLE 1

|  | % Space | % DBM |
|---|---|---|
| U.S. Pat. No. 5,507,813 | 37.2 | 62.8 |
| Osteoimplant of Example 2 | 26.0 | 74.0 |

COMPARATIVE EXAMPLE 2

The thickness and density of a 2 cm×4 cm sheet of a shaped material prepared according to U.S. Pat. No. 5,507,813 and Example 2 above was measured. This was repeated for three samples of each. The results are contained in Table 2 below.

TABLE 2

| Sample | Thickness (mm) | Weight (g) | Density (g/cm$^3$) |
|---|---|---|---|
| U.S. Pat. No. 5,507,813 | | | |
| 1 | 2.21 | 1.37 | 0.775 |
| 2 | 2.54 | 1.46 | 0.719 |
| 3 | 2.54 | 1.38 | 0.679 |
| Average | 2.43 | 1.40 | 0.724 |
| Osteoimplant of Example 2 | | | |
| 1 | 1.45 | 1.14 | 0.983 |
| 2 | 1.20 | 0.89 | 0.927 |
| 3 | 1.31 | 1.13 | 1.078 |
| Average | 1.32 | 1.05 | 0.996 |

COMPARATIVE EXAMPLE 3

Test articles of the shaped material of U.S. Pat. No. 5,507,813 and the material of Example 2 above were prepared. Rectangular strips of the material of Example 2 approximately 25 mm wide and 60 mm long were press-cut from a large sheet of material. The shaped material of U.S. Pat. No. 5,507,813 was already manufactured to these approximate dimensions before testing. The shaped material of U.S. Pat. No. 5,507,813, the material of Example 2, and stacked sheets (3 to 5) of the material of Example 2 (approximating the thickness of the shaped material of U.S. Pat. No. 5,507,813) were cut to approximately 50 mm in length.

The final pretest width and thickness of each test article was measured at its center using a Mitutoyo Model 500-196CE digital caliper and a Mitutoyo Model 7301 0.01 mm–10 mm dial thickness gage respectively. For the stacked shaped material of Example 2 test articles, the dimensions of the entire stack was recorded and used for calculations. Tensile tests were performed on the test articles.

A uniaxial servo-hydraulic test machine (MTS model 858 Bionix) was used under displacement control to apply a constant tensile displacement to the test articles at a rate of 5 mm/min. In all cases, failure (a peak in load, followed by a sharp drop in load) was observed before 6 mm of tensile displacement was reached. The gage length (in these tests, the initial distance between the grips) was set to be 31.34 mm. The test article holding fixtures consisted of two vise-like grips, which were hand-tightened to attach each test specimen to the load cell (lower grip) and to the actuator (upper grip). A 200 lbf. load cell, operating in the 20 lbf. load range was used to record load levels for all tests. For some of the single sheets of the material of Example 2 and stacked sheets of the material of Example 2 tests, a 50 HZ low-pass filter was enabled to reduce high frequency component noise in the load signal. Load and displacement data were collected at a sampling rate of 20 Hz for the duration of each test. Form is as packaged. All Tests were performed on the material without subsequent rehydration Specimen dimensional data was used to calculate each test article's initial cross sectional area, which was then used to calculate tensile engineering stress values from gathered data. This information, along with actuator displacement data, allowed tensile engineering stress-strain curves to be calculated for each test article. Elastic modulus was also calculated or extracted from the data and is given in Table 3 below.

TABLE 3

|   | A (mean ± SD) | B (mean ± SD) | C (mean ± SD) |
| --- | --- | --- | --- |
| Ultimate Strength | 1.21 ± 0.70 N | 2.48 ± 0.61 N | 46.17 ± 5.29 N |
| Modulus of Elasticity | 0.54 ± .015 Mpa | 0.29 ± 0.08 MPa | 3.34 ± 0.97 MPa |
| Ultimate Displacement | 3.23 ± 0.57 mm | 3.97 ± 1.26 mm | 3.34 ± 0.97 mm |

Key
A: Single Layer of the Material of Example 2
B: Multi Layer of the Material of Example 2
C: The Shaped Material of U.S. Pat. No. 5,507,813

COMPARATIVE EXAMPLE 4

50 grams of dry, mineralized bone fibers were prepared as the osteoimplant of Example 2 wherein the biocompatible fluid carrier was a 50% (wt) Glycerol/water. Another three portions, each containing 50 grams of dry, mineralized bone fibers from the same source were processed according to the method of U.S. Pat. No. 5,507,813. A measurement of the area of the finished osteoimplant as well as its weight after lyophilization and its thickness of three places was made. The results are contained in Table 4 below.

TABLE 4

| Sample | Starting WT. (g) | Area (cm²) | Thickness 1 (mm) | Thickness 2 (mm) | Thickness 3 (mm) |
| --- | --- | --- | --- | --- | --- |
| A | 50 | 567 | 0.6 | 0.45 | 0.68 |
| $C_1$ | 50 | 100 | 2.05 | 2.62 | 2.12 |
| $C_2$ | 50 | 100 | 2.05 | 1.94 | 2.15 |
| $C_3$ | 50 | 100 | 1.65 | 1.7 | 1.78 |

Key:
A -Sample prepared as in Example 2 above.
$C_{1-3}$ -The shaped material of U.S. Pat. No. 5,507,813 prepared following standard operating procedure.

COMPARATIVE EXAMPLE 5

10 cm long specimens of the shaped material of Example 2 (A) and the shaped material of U.S. Pat. No. 5,507,813 (C) were fixed in a gripping device at different heights (1–8 cm). The portion of the material extending from the fixture was bent over to 90 degrees, and the spring back was measured (relative to the original, unbent position) using a protractor. The results are contained in Table 5 below.

TABLE 5

The shaped material of U.S. Pat. No. 5,507,813 prepared following standard operating procedure.

| Pinch Point | Degree Bend | Bone Return |
| --- | --- | --- |
| 8 cm | 90 | Back to 30 degrees |
| 7 cm | 90 | Back to 25 degrees |
| 6 cm | 90 | Memory to 25 degrees |
| 5 cm | 90 | Memory to 30 degrees |
| 4 cm | 90 | Memory to 20 degrees |
| 3 cm | 90 | Memory to 20 degrees |
| 2 cm | 90 | Memory to 15–20 degrees |
| 1 cm | 90 | Memory to 15–20 degrees |
| Sample prepared as in Example 2 above | | |
| 8 cm | 90 | No memory |
| 7 cm | 90 | No memory |
| 6 cm | 90 | No memory |
| 5 cm | 90 | No memory |
| 4 cm | 90 | No memory |
| 3 cm | 90 | No memory |
| 2 cm | 90 | Memory to 85 degrees (limp) |
| 1 cm | 90 | Memory to 15 to 10 degrees |

What is claimed is:

1. A method of forming an osteogenic osteoimplant having not greater than 32% void volume, the method comprising:

providing a coherent mass of bone particles optionally in combination with one or more biocompatible components, the coherent mass formed at least in part from elongate bone-derived elements optionally in combination with bone powder; and, mechanically shaping the coherent mass of bone particles to form the osteogenic osteoimplant.

2. The method of claim 1 wherein the bone particles are obtained from cortical, cancellous and corticocancellous bone of autogenous, allogenic, xenogenic and transgenic origin.

3. The method of claim 1 wherein the biocompatible component is selected from the group consisting of biocompatible fluid carrier, biocompatible binder, filler, fiber, mesh, substance providing radiopacity, plasticizer, biostatic/biocidal agent, surface active agent, and bioactive substance.

4. The method of claim 1 which further comprises applying heat to the composition before, during or after mechanically shaping the coherent mass.

5. The method of claim 1 which further comprises cross-linking bone particles within the composition before, during or after mechanically shaping the coherent mass.

6. The method of claim 1 which further comprises dehydrating the composition before, during or after mechanically shaping the coherent mass.

7. The method of claim 4 which further comprises dehydrating the heated, mechanically shaped coherent mass after applying the heat.

8. The method of claim 1 wherein the step of mechanically shaping comprises pressing, extruding and/or rolling.

9. The method of claim 8 further comprising means for the application of compressive force.

10. The method of claim 9 wherein the compressive and a lateral force are applied simultaneously.

11. The method of claim 1 further comprising the step of placing the coherent mass between two flexible stick-resistant surfaces prior to the step of mechanically shaping.

12. The method of claim 1 further comprising the step of placing the coherent mass of bone-derived particles on an inflexible, impermeable, horizontally planar work surface prior to the step of mechanically shaping.

13. The method of claim 12 wherein the step of mechanically shaping further comprises contacting the coherent mass with at least one revolving cylindrical roller.

14. The method of claim 13 wherein said at least one revolving cylindrical roller is modified to provide for the surface treatment of one or both surfaces of the osteoimplant.

15. The method of claim 1 further comprising the step of:
occluding a portion of the surface area of the osteoimplant to provide at least one zone of impermeability to soft tissue ingrowth wherein said zone is integral with the osteoimplant.

16. The method of claim 15 wherein the occluding step comprises heating a portion of the surface area at elevated temperature.

17. The method of claim 15 wherein the occluding step comprises crosslinking bone particles at a portion of the surface area of the mechanically shaped mass.

18. The method of claim 1 further comprising the step of shaping the osteoimplant to a determined form, configuration and/or three-dimensional architecture.

19. The method of claim 1 further comprising the step of layering and fastening the osteoimplant to form a laminate material.

20. The method of claim 1, comprising the additional step of
controlling the coherent mass and mechanical shaping thereof to ensure the thus-formed osteoimplant possesses not greater than 32% void volume.

21. The method of claim 20, comprising the additional step of
controlling the coherent mass and mechanical shaping thereof to ensure the thus-formed osteoimplant possesses a density greater than about 0.8 g/cm$^3$.

22. The method of claim 20, comprising the additional step of
providing the coherent mass in the form of a flexible sheet comprising elongate bone particles.

23. The method of claim 22, comprising the additional step of
providing the coherent mass with at least about 60% by weight of the elongate bone particles possessing a median length of from about 2 to about 200 mm., a medium thickness of from about 0.05 to about 2 mm and a median width of from about 1 mm to about 20 mm with the chosen median length being greater than the chosen median width.

24. The method of claim 23, wherein at least about 60% by weight of the elongate bone particles possess a median length of from about 10 to about 100 mm, a median thickness of from about 0.2 to about 1 mm and a median width of from about 2 to about 5 mm.

25. The method of claim 22, comprising the additional step of
providing the coherent mass with at least about 60% by weight of the elongate bone particles possessing a median length to median thickness ratio of from about 50:1 to about 500:1, and a median length to median width ratio of from about 10:1 to about 200:1.

26. The method of claim 25, wherein at least about 60% by weight of the elongate bone particles possess a median length to median thickness ratio of from about 50:1 to about 100:1, and a median length to median width ratio of from about 50:1 to about 100:1.

27. The method of claim 22 comprising the additional step of
entangling the elongate bone particles to cause them to mechanically adhere to one another.

28. The method of claim 22, comprising the additional step of shaping the implant as a sheet, plate, disk, tunnel, cone or tube.

* * * * *